(12) United States Patent
Stein et al.

(10) Patent No.: US 6,351,992 B1
(45) Date of Patent: Mar. 5, 2002

(54) DEVICE AND A MEASURING METHOD FOR MEASURING THE EXTENSION OR CONTRACTING PROPERTIES OF FILAMENTOUS SPECIMENS

(75) Inventors: Wolfgang Stein, Moenchengladbach; Ulrich Moerschel, Linnich, both of (DE)

(73) Assignee: Textechno Herbert Stein GmbH, Moenchengladbach (DE)

( * ) Notice: Subject to any disclaimer, the term of this patent is extended or adjusted under 35 U.S.C. 154(b) by 0 days.

(21) Appl. No.: 09/576,600

(22) Filed: May 24, 2000

(30) Foreign Application Priority Data

May 29, 1999 (DE) .......................... 199 24 637

(51) Int. Cl.⁷ ............................... G01L 5/04
(52) U.S. Cl. ........................................ 73/160
(58) Field of Search .................. 73/159, 160, 796, 73/826, 828

(56) References Cited

U.S. PATENT DOCUMENTS

| | | | | |
|---|---|---|---|---|
| 3,683,846 A | * | 8/1972 | Flournoy et al. | 118/33 |
| 4,393,701 A | * | 7/1983 | Lawson | 73/160 |
| 5,233,200 A | * | 8/1993 | DiMarcello et al. | 250/559.29 |
| 5,737,815 A | * | 4/1998 | Le | 28/250 |
| 5,983,619 A | * | 11/1999 | Tone | 57/264 |

OTHER PUBLICATIONS

"Continuous Tester"—reprinted from Textile Asia, Mar. 1981.

* cited by examiner

Primary Examiner—Max Noori
(74) Attorney, Agent, or Firm—Diller, Ramik & Wight

(57) ABSTRACT

In an apparatus for measuring the extension and contraction properties of filamentous specimens (10), comprising a housing (2) with at least two delivery devices (4, 8) between which a test section (12) for the filamentous specimen (10) extends, a force sensor (14) measuring the force exerted on the filamentous specimen (10) in the test section (12), and a heating means (18) enclosing the filamentous specimen (10) in the test section (12) and heating it to a predetermined temperature, it is provided that a positioning means (24) displaces the filamentous specimen (10) relative to the heating means (18) or displaces the heating means (18) relative to the filamentous specimen (10) such that, in one end position, the specimen (10) is placed outside the heating means (18) and, in the other end position, the specimen is within the heating means (18).

22 Claims, 3 Drawing Sheets

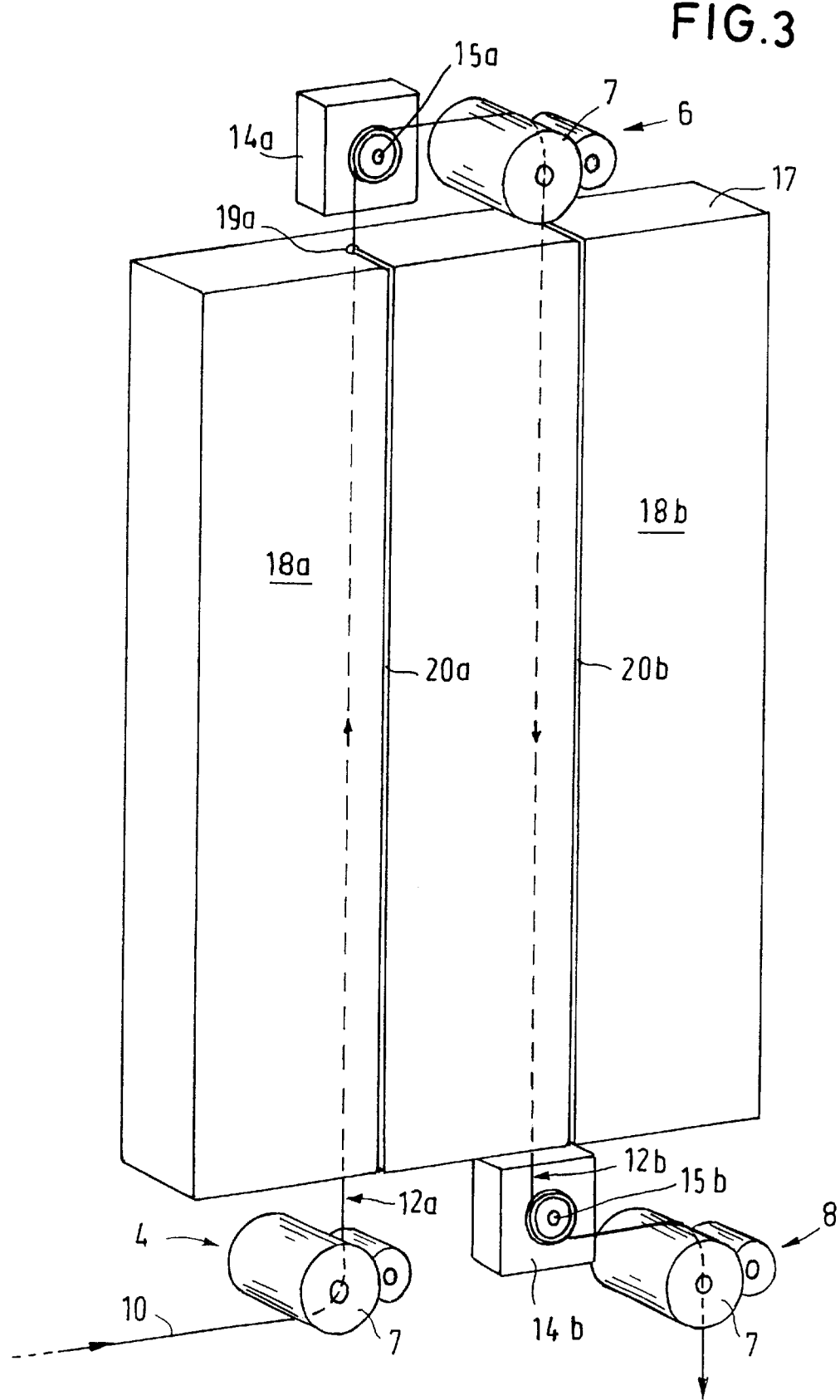

DEVICE AND A MEASURING METHOD FOR MEASURING THE EXTENSION OR CONTRACTING PROPERTIES OF FILAMENTOUS SPECIMENS

BACKGROUND ART

The present invention refers to a device and a method for measuring the extension or contraction properties of filamentous specimens.

Such testing apparatus are known, for example, under the name "Dynafil" and are available from Textechno, Mönchengladbach Germany (Textile Asia, March 1981, Business Press Limited: Continuous Tester). In these testing apparatus, the filamentous specimens are supplied through a heating tube under adjustable extension or overfeed (shortening) that is constant throughout the test or without an alteration in length, the occurring tensile force being continually measured. Depending on the test parameters set and on the type of specimen, various test methods may be obtained:

draw force test of pre-oriented or fully stretched yarns, crimp force test of textured yarns, and shrinkage force test of flat and textured yarns.

Another known testing apparatus by the name TYT, available from Lawson Hemphill, continually measures the alterations in length of a filament yarn under constant tensile force while the yarn passes through a closed heating tube. Preferably, this test is used to determine the crimp contraction of textured yarns.

The known apparatus comprise a test section formed by an inlet and an outlet delivery device and the intermediately arranged heating tube, as well as the force sensor (DYNAFIL) or the device for keeping the filament tensile force constant (TYT). The supply rates of both delivery devices may be varied in common or relative to each other.

The melting temperature of the fiber materials usually subjected to such tests is 260° C. at maximum (polyester, nylon 6.6). Therefore, the heating tube temperature of the known test apparatus must always be set below this limit value. Otherwise the yarn would melt and tear in the heating tube when the apparatus is at a standstill or running slowly, as well as when a new specimen is introduced into the test section.

Due to this limitation of the heating tube temperature, the maximum possible filament speeds, at which the yarn is still heated to the degree necessary for the test, are limited, too. Depending on the count of the yarn, 100 to 200 m/min can be reached.

SUMMARY OF THE INVENTION

Starting from this prior art, it is an object of the present invention to improve testers of the type mentioned above such that, on the one hand, substantially higher test speeds are possible and, on the other hand, high temperature resistant specimens can be tested.

Advantageously, the invention provides that a positioning means displaces the filamentous specimen relative to the heating means or the heating means relative to the filamentous specimen such that, in an end position, the specimen is placed within the heating means and, in the other end position, the specimen is placed outside the heating means.

To this effect, the heating means is not designed as a closed tube as with conventional testers. Rather, it comprises a heating channel with a lateral slot for inserting and removing the specimen, the slot being adapted to be opened and closed automatically.

Such a positioning means in connection with the heating means allows for heating temperatures far above the melting temperatures of the fiber materials, e.g. up to 800° C., and thus much higher filament speeds, e.g. up to 1000 m/min, at which the filament reaches the optimum temperature. When the running of the filamentous specimen is to be stopped or a new specimen is to be placed into the test section, the positioning means first moves the specimen—still running at a high speed—out of the heating means. Upon restarting the device, the specimen is first accelerated to the test speed outside the heating means and introduced into the heating channel thereafter. In this manner, melting and tearing of the fibre material in the heating means are excluded.

Another advantage of such a high-temperature heating means is that it also allows for the testing of high-temperature resistant fiber materials. Testing such materials in the known apparatus at relatively low heating temperatures does not yield any useful test results.

The delivery devices of the present tester may be motor-driven godets or feed rollers with aprons or nip rolls.

In a development of the invention, it is provided that additional measuring means are arranged in the test section between the inlet and the outlet delivery device, in front of the inlet delivery device, seen in the running direction of the specimen, or behind the outlet delivery device. These additional measuring means serve to measure friction, filament breaks, entanglements, yarn evenness or yarn count.

In a preferred embodiment, it is provided that a means for adjusting and maintaining constant a predetermined pre-tensioning force in the running specimen is arranged in front of the first delivery device, seen in the running direction of the specimen, which may be controlled by the measuring signal from the force sensor picked from the test section. This means ensures an exactly adjustable pre-tensioning force constant during the test.

Behind the heating means, seen in the running direction of the specimen, a temperature sensor may be disposed for determining the actually reached specimen temperature. This temperature sensor provides a measuring signal suitable for the temperature control of the heating means.

Further, behind the heating means, seen in the running direction of the specimen, a twisting means for generating a false twist in the specimen may be provided.

The device of the present invention joins the different test methods of the known test apparatus in one apparatus. In measuring the running filamentous specimen, tests with constant extension or contraction of the specimen and a simultaneous measuring of the force occurring in the specimen become possible. Alternatively, the test may be effected using a constant tensile force acting on the specimen, the speed of at least one of the two delivery devices being continually adjusted. The variation in length of the specimen, which at all times corresponds to the difference in speed between the two delivery devices, is measured continually.

At heating temperatures below the melting temperature of the specimen, testing of the standing specimen is also possible. Here—after insertion of the specimen into the tester—either without change in length or with a constant change in filament length, force is measured in relation to time, or, with the force maintained constant, the change in length is measured in relation to the time.

In measurements of the standing specimen, an essential advantage of the present invention is that a subsequent measurement may be effected very fast by introducing a new specimen section by means of the delivery devices.

BRIEF DESCRIPTION OF THE DRAWINGS

The following is a detailed description of embodiments of the present invention, taken in conjunction with the accompanying drawings.

In the figures:

FIG. 3 illustrates a second embodiment.

DETAILED DESCRIPTION OF PREFERRED EMBODIMENTS

Figure 1:
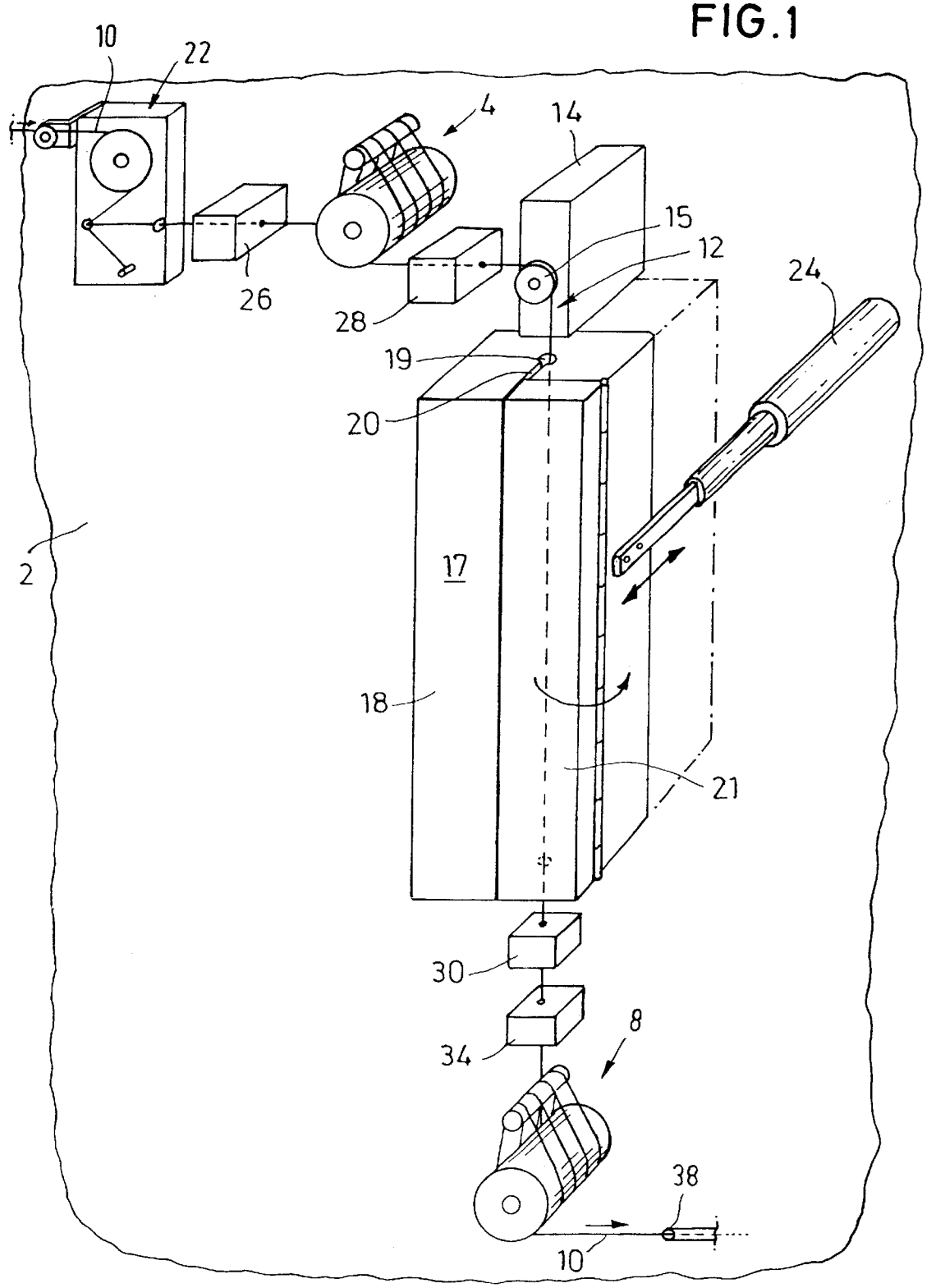
FIG. 1 is a partial view of the present tester.

Referring now to the figures, FIG. 1 shows a tester for tensile force or length variation tests of filamentous specimens 10, arranged in a housing 2. The specimen 10 can be tested with the specimen standing or running. The tester has at least two delivery devices 4, 8 which, as is obvious from FIG. 1, may be godets or feed rollers with aprons or nip rolls 7. Each delivery device 4,18 is driven by a precision motor that has a variable speed regulation and a speed measuring feature (e.g. incremental transmitter, resolver or tachometer generator).

Figure 2:
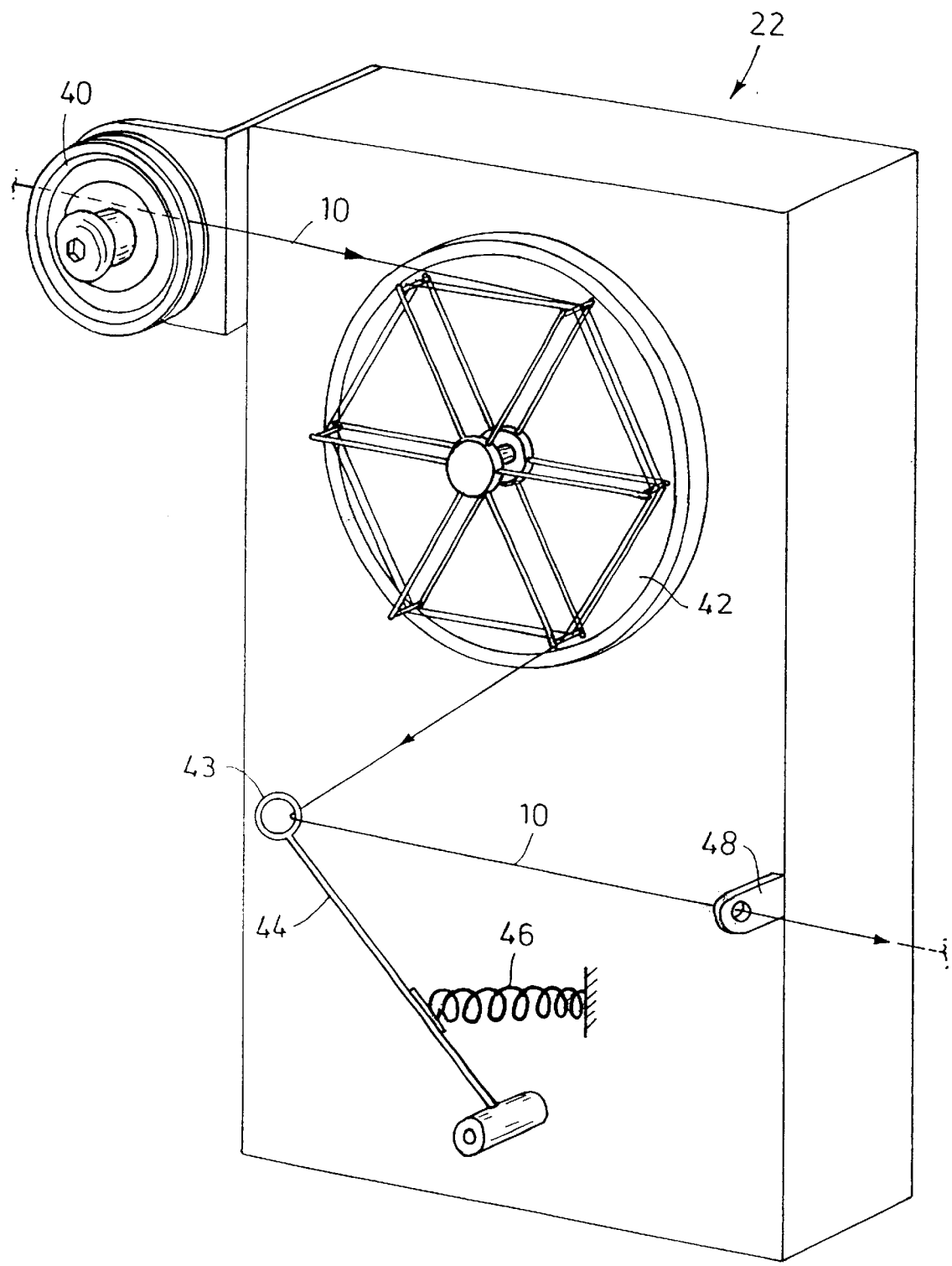
FIG. 2 illustrates a means for setting pre-tension.

In front of the inlet delivery device 4, a unit 22 is arranged for maintaining constant a predetermined pre-tensioning force in the running specimen 10, as illustrated in FIG. 2. This means 22 may be adjusted pneumatically or electronically, the means being controllable by the measuring signal from the force sensor 14 picked at the specimen 10. The means 22 is set with both delivery devices 4, 8 running at the same speed, i.e. without delay, until the force measured by the force sensor 14 matches the pre-tensioning force to be set.

The means 22 comprises an inlet-side disk-tensioner 40 via which the specimen 10 is supplied. The specimen 10 is wound upon a reel, at least two complete windings being on the reel 42. From the motor driven reel 42, the specimen is passed through an eyelet 43 in a feeler lever 44 and via an outlet-side guiding eyelet 48 to a measuring means 26 or the inlet delivery device 4, respectively. The feeler lever 44 is pre-tensioned by means of a pressure spring 46. The spring force of the pressure spring 45 may be adjusted manually or electronically depending on a control signal so that a desired pre-tensioning force may be set in the specimen 10. The position of the feeler lever 44 controls the motor drive of the reel 42 so that an exactly constant pre-tensioning force acts on the specimen 10.

As an alternative to the means 22 and prior to the beginning of a test, the ratio of the speeds of the inlet and the outlet delivery devices 4, 8 may be altered, first with the specimen running, such that the tensioning force in the test section 12 reaches the desired value for the pre-tensioning force. The speed ratio thus determined is to be considered when the tensioning force or the change in length of the specimen 10 is set for the actual measurement.

A test section 12 for the filamentous specimen 10 extends between the delivery devices 4, 8. In the test section 12, a force sensor 14 is provided with which the tensile force in the specimen 10 can be measured. The changes in length of the specimen 10 in the test section 12 are determined from the speed differences between the delivery devices 4, 8. The specimen is deflected in the test section by a filament guiding roller 15 mounted to the force sensor 14 and then enters a heating channel 19 of a heating means 18. On the side of the heating channel 19 averted from the housing 2, a slit 20 is provided in the housing 17 of the heating means 18 through which the specimen 10 may be guided out of the heating channel 19. Thus, in the embodiment illustrated in FIG. 1, the heating means 18 is at least partly retractable into the housing 2 by means of a positioning means 24, whereby the specimen 10 can be guided completely out of the heating channel 19 by withdrawing the heating means.

The housing 17 of the heating means 18 has a mechanically operated pivoting flap 21 which is closed when the heating means 18 is fully withdrawn or fully moved, and which is opened automatically, as soon as the heating means 18 is to be displaced. In the closed position, the pivotable flap 21 avoids too great heat losses.

As an alternative, it is also possible, with the heating means 18 stationarily fixed to the housing 2, to displace the delivery devices 4, 8 together with the measuring means 14 in parallel until the test section 12 is outside the heating channel 19.

According to another alternative, the heating means 18 and the delivery devices 4,8, including the measuring means 14, may be fastened stationary at the housing 2, with only the specimen 10 in the test section 12 being guided out of or into the heating channel 19 by means of filament guiding means.

Due to the fast introduction of the specimen 10 into the heating channel 19, as well as the fast removal by means of the positioning means 24, it is possible to operate the heating means 18 at temperatures up to an upper limit of 800° C. and more. This allows for test speeds of more than 1000 m/min. Here, the heating temperature may be set steplessly from ambient temperature to a desired temperature in the heating channel 19. Moreover, tests of high-temperature resistant fibre materials can be carried out.

FIG. 1 illustrates additional measuring means 26, 28 that may be disposed in front of, in or behind the test section 12. These additional measuring means 26, 28 serve to measure friction, filament breaks, entanglements, bulk of textured yarns, yarn evenness or yarn count.

Behind the heating means 18, seen in the running direction of the specimen, a temperature sensor 30 may be disposed at the lower end of the heating channel 19, for determining the actually reached specimen temperature. The temperature signal may be used for heating control and/or control of the transport speed of the delivery devices 4, 8.

Further, behind the heating means 18, seen in the running direction of the specimen, a twisting means 34 for generating a false twist in the specimen 10 may be provided.

Behind the outlet delivery device 8, the specimen 10 may be transported off and cleared by means of a suction means 38.

Using the tester described above, the following measurements may be carried out, for example:

Measurement under constant application of force to the specimen

In this case, a predetermined constant tensile force is set using varying speed ratios of the delivery devices 4, 8, and the resulting extension or contraction of the specimen is measured under the effect of a predetermined temperature. The extension/contraction measurements are effected by measuring the difference in speed between the delivery devices 4, 8.

Measuring the tensile force at a constant change in the specimen length

Here, a predetermined extension or contraction is applied by a constant speed difference of the delivery devices 4, 8. The respective resulting tensile force is measured and recorded, with the measurements possibly being carried out at different temperatures in the heating channel and at different transport speeds.

Dynamic force-extension tests

The speed ratios of the two delivery devices may also be altered under program control during the test. Thus, dynamic force-extension graphs may be measured, for example, by incrementally or continuously increasing the extension and measuring the resulting (drawing) force, which is recorded as a function of the extension. Here, the extension of the specimen 10 is set via the different transport speeds of the delivery devices 4, 8.

Force or length variation measurement with increasing filament speed of the specimen To determine suitable parameters regarding the temperature in the heating channel 19 and the specimen speed for the above measurements, preliminary tests of the extension and contraction properties of the specimen 10 may effected with force or length variation measurements at increasing filament speed and constant temperature in the heating channel 19.

FIG. 3 illustrates another embodiment, wherein the specimen 10 may be supplied to a first test section 12a via a first supply unit 4, the test section extending in a heating channel 19a of a first heating means 18a. At the end of the first test section 12a, the specimen 10 is supplied to a second supply unit 6 via a filament guiding roller 15a of a first force sensor 14a, associated with the first test section, the specimen 10 being introduced into a second test section 12b via the second supply unit. 12a The second test section 12b extends in a heating channel 19b of a second heating means 18b. The second test section 12b includes a second force sensor 14b at which the specimen 10 is supplied to a third supply unit 8 via a guiding roller 15b.

The supply units 4, 6, 8 of this embodiment are either godets or feed rollers with aprons or nip rolls 7. Both heating means 18a, 18b have a slit 20a, 20b, respectively, through which the specimen 10 may be introduced into the heating channel 19a, 19b. It is evident that the slits 20a, 20b may be closed as in the embodiment of FIG. 1. For example, the slits 20a, 20b may be closed separately or together by a flap adapted to be displaced in parallel or pivoted.

The device of FIG. 3 is particularly suited for drawing filament cables or coarse filament strands of 10,000 to 20,000 dtex.

Here, the specimen 10 may be pre-stretched in the first test section 12a and the final drawing may be done in the second test section 12b.

Also in this embodiment, the housing 17 with the heating means 18a, 18b may alternatively be retracted into the housing 2, or, as an alternative thereto, the filamentous specimen 10 may be guided out from the heating means 18a, 18b with parallel displacement.

What is claimed is:

1. An apparatus for measuring the extension and contraction properties of filamentous specimens (10) comprising a housing (2), at least two delivery devices (4, 6, 8), a test section (12; 12a, 12b) for the filamentous specimen (10) located between the delivery devices (4, 6, 8), force sensor mean (14; 14a, 14b) for measuring the force exerted on the filamentous specimen (10) in the test section (12), heating means (18; 18a 18b) for enclosing the filamentous specimen (10) in the test section (12; 12a, 12b) and heating the filamentous specimen (10) to a predetermined temperature, and positioning means (24) for displacing one of the filamentous specimen (10) and the heating means (18; 18a, 18b) relative to each other between first and second positions such that in the first position the filamentous specimen (10) is located outside the heating means (18; 18a, 18b) and in the second position the filamentous specimen (10) is located inside the heating means (18; 18a, 18b).

2. The apparatus as defined in claim 1 including means for adjusting an upper limit of the heating temperature of the heating means (18; 18a, 18b) within a range from more than 260° C. to 800° C.

3. The apparatus as defined in claim 1 wherein the heating means (18; 18a, 18b) includes a housing (17), a longitudinally extending heating channel (19; 19a, 19b) in said housing (17) housing the filamentous specimen (10) in said second position, and the housing (17) further includes a slit (20; 20a, 20b) opening into the heating channel (19; 19a, 19b) for introducing the specimen (10) into the heating channel (19; 19a, 19b) during the operation of said positioning means (24).

4. The apparatus as defined in claim 3 including means for closing the slit (20; 20a, 20b).

5. The apparatus as defined in claim 1 including additional measuring means (26, 28) arranged at least at one of between the delivery devices (4, 6, 8), upstream of the delivery devices (4, 6, 8) and downstream of the delivery devices (4, 6, 8).

6. The apparatus as defined in claim 4 wherein said additional measuring means measures at least one of filament friction, breaks and entanglements and textured yarn bulk, evenness and count.

7. The apparatus as defined in claim 6 including means (22) for adjusting and maintaining constant a predetermined pre-tensioning force in the filamentous specimen (10) located in front of a first (4) of the delivery devices (4, 6, 8) controlled by a signal from said force sensor means (14; 14a, 14b).

8. The apparatus as defined in claim 1 including temperature sensor means (30) associated with the heating means (18; 18a, 18b) for determining the actual temperature of the filamentous specimen (10).

9. The apparatus as defined in claim 1 including twisting means (34) for creating a false twist in the filamentous specimen (10).

10. The apparatus as defined in claim 1 wherein said delivery devices (4, 6, 8) include an inlet delivery device (4; 6) and an outlet delivery device (6; 8), and program control means for independently controlling the operation of said inlet and outlet delivery devices (4; 6 and 6; 8).

11. The apparatus as defined in claim 10 wherein said program control means is operative to continually change the transport speed ratio of the inlet and outlet delivery devices (4; 6 and 6; 8) whereby a constant tensile force can be set in the filamentous specimen (10), and said force sensor means (14) generate a measuring signal for controlling the transport speed ratio.

12. The apparatus as defined in claim 10 wherein the program control means is operative to effect a constant change in the length of the filamentous specimen (10) with a simultaneous measurement of the tensile force through control of the transport speed ratio of the delivery devices (4, 6, 8).

13. The apparatus as defined in claim 12 wherein the program control means is effective through an extension acting on the filamentous specimen (10) for generating dynamic force information.

14. The apparatus as defined in claim 1 including program control means for varying the temperature of the heating means (18; 18a, 18b) during at least one of tensile force and length measurement of the filamentous specimen (10).

15. The apparatus as defined in claim 1 wherein said delivery devices (4, 6, 8) include three individual delivery devices, said test section (12; 12a, 12b) includes two separate test sections (12a, 12b), and said heating means (18;

18a, 18b) includes an individual heating means (18a, 18b) associated with the respective separate two test sections (12a, 12b).

16. The apparatus as defined in claim 15 wherein each separate test section (12a, 12b) is associated with a respective separate force sensing means (14a, 14b).

17. A method of measuring the extension or contraction properties of a filamentous specimen comprising the steps of feeding the filamentous specimen along a path of travel having an inlet end, an outlet end and a test path portion between the inlet and outlet ends, pretensioning the filamentous specimen, displacing one of heating means and the filamentous specimen laterally with respect to the test path portion for introducing the filamentous specimen into and for removing the filamentous specimen from the heating means, heating the filamentous specimen by the heating means, and measuring at least one of the tensile force and length of the filamentous specimen.

18. The method as defined in claim 17 including the step of maintaining a constant extension of the filamentous specimen by maintaining a fixed transport speed ratio at the inlet end and at the outlet end of the path of travel.

19. The method as defined in claim 18 including the step of varying the extension of the filamentous specimen at least one of incrementally and continually to measure dynamic force-extension.

20. The method as defined in claim 17 including the step of maintaining a constant tensile force on the filamentous specimen by maintaining a variable speed ratio of the filamentous specimen at the inlet and outlet ends thereof.

21. The method as defined in claim 17 wherein the test path portion includes two separate test paths through which the filamentous specimen is fed, and selectively variably heating the filamentous specimen along each separate test path.

22. The method as defined in claim 21 including the step of respectively pretensioning and final tensioning the filamentous specimen during feeding thereof along the separate test paths.

* * * * *